(12) United States Patent
Rand

(10) Patent No.: US 6,792,077 B2
(45) Date of Patent: Sep. 14, 2004

(54) COLLIMATION SYSTEM FOR DUAL SLICE EBT SCANNER

(75) Inventor: Roy E. Rand, Palo Alto, CA (US)

(73) Assignee: GE Medical Systems Global Technology Company, LLC, Waukesha, WI (US)

(*) Notice: Subject to any disclaimer, the term of this patent is extended or adjusted under 35 U.S.C. 154(b) by 45 days.

(21) Appl. No.: 10/064,182

(22) Filed: Jun. 19, 2002

(65) Prior Publication Data
US 2003/0235271 A1 Dec. 25, 2003

(51) Int. Cl.[7] .................................. G21K 1/02
(52) U.S. Cl. ........................ 378/149; 378/147
(58) Field of Search .................. 378/147, 149, 378/150, 4, 9, 10, 19, 21

(56) References Cited

U.S. PATENT DOCUMENTS

| | | | |
|---|---|---|---|
| 4,352,021 A | | 9/1982 | Boyd et al. |
| 4,531,226 A | * | 7/1985 | Peschmann .................. 378/143 |
| 4,610,021 A | * | 9/1986 | Peschmann et al. ......... 378/150 |
| 5,442,673 A | * | 8/1995 | Rand et al. .................... 378/10 |
| 6,118,839 A | | 9/2000 | Dafni et al. ................... 378/15 |
| 6,275,562 B1 | | 8/2001 | He et al. ....................... 378/19 |

* cited by examiner

Primary Examiner—Edward J. Glick
Assistant Examiner—Chih-Cheng Glen Kao
(74) Attorney, Agent, or Firm—McAndrews, Held & Malloy, Ltd.; Peter J. Vogel; Michael A. Dellapenna

(57) ABSTRACT

An electron beam tomography (EBT) scanning system comprising an electron source generating an electron beam, a target ring that receives the electron beam and emits an x-ray fan beam upon impingement of the electron beam on the target ring, a pair of detector arrays arranged opposite the target ring, and a collimator arranged concentrically between the target ring and the pair of detector arrays. The collimator has interior and exterior walls concentrically arranged with one another and surrounding a patient examination area. The interior and exterior walls have a first set of apertures aligned to collimate the x-ray fan beam into a first collimated beam having a first width and a second collimated beam having a second width. Each collimated beam may form a single or double tomographic slice. The collimated beams are detected by the pair of detector arrays.

19 Claims, 4 Drawing Sheets

COLLIMATION SYSTEM FOR DUAL SLICE EBT SCANNER

BACKGROUND OF INVENTION

Certain embodiments of the present invention generally relate to an electron beam tomography system, and more particularly to a collimator for a dual-slice electron beam tomography system.

Computerized tomography (CT) systems produce planar images along imaginary cuts, or slices, through a patient. CT systems typically include an x-ray source, which revolves about an imaginary axis through a subject. After passing through the subject, the x-rays impinge on an opposing array of detectors.

Typical CT patient scans are executed in either an axial mode or in a helical mode. In axial mode, the table that supports the patient stops, the scan is executed, and then the table moves to a new location. In helical mode, the patient table continuously moves throughout the course of the scan. Single slice scanners (scanners having one detector array) are common, and dual slice CT systems (systems having two detector arrays) are known.

Some CT scanners include a scanning electron beam x-ray source, such that an electron beam is magnetically deflected so as to rotate in a generally arcuate path, and in doing so, impinges upon an arc-shaped target. As the electron beam impinges on the target, a source of x-rays is generated. As the electron beam moves, so does the source of x-rays. The x-rays encounter a collimator which passes a portion and blocks a portion of the x-rays. The x-rays are shaped into a fan beam by the collimator and then intercepted by a ring-shaped detector array on an opposite side of the patient. U.S. Pat. No. 4,352,021 ("the '021 patent"), issued Sep. 28, 1982, discloses such an electron beam scanner. However, in order to collimate the x-ray fan beam at different widths, multiple collimators having different sized apertures were typically needed, thereby increasing the cost of the system.

U.S. Pat. No. 5,442,673, issued Aug. 15, 1995 ("the '673 patent"), discloses an x-ray collimator for use within an electron beam computed tomography (EBT) scanner, in which a rotating electron beam is directed to impinge upon a ring shaped target. The '673 patent discloses variable tomographic slice width for a single slice EBT system. Single slice EBT systems, however, take longer to scan a given number of slices than corresponding dual slice systems.

Thus, a need exists for a more efficient method and apparatus for achieving EBT scanning.

SUMMARY OF INVENTION

Embodiments of the present invention provide an electron beam tomography (EBT) scanning system comprising an electron source, a target ring, first and second detector arrays, and a collimator. The electron source generates an electron beam, which is received by the target ring. The target ring emits an x-ray fan beam upon impingement of the electron beam on the target ring. The first and second detector arrays are arranged opposite the target ring and detect the x-ray fan beam. The collimator is arranged concentrically between the target ring and the first and second detector arrays. The collimator has interior and exterior walls concentrically arranged with one another and surrounding a patient examination area. The interior and exterior walls have first and second sets of apertures. The first set of apertures are aligned to collimate the x-ray fan beam into a first collimated beam having a first width. The first collimated beam may be detected by first and second detector arrays when the collimator is in a first position. The first collimated beam may be detected by one of the first and second detector arrays when the collimator and detector are moved to a second position. The second set of apertures are aligned to collimate the x-ray fan beam into a second collimated beam having a second width. The second collimated beam may be detected by the first and second detector arrays when the collimator is moved to a third position. The collimator is moved between the first, second, and third positions with respect to the target ring to define the first and second collimated beams having the first and second widths, respectively.

The collimator also includes a detector-only region, a source-only region and a source/detector overlap region. The detector-only region has a first set of post-patient x-ray apertures for shielding the detector from scattered x-rays when the beam has a first width; and a second set of post-patient x-ray apertures for shielding the detector from scattered x-rays when the beam has a second width. The source/detector overlap region has a first set of pre-patient x-ray apertures for collimating the x-ray fan beam into the first collimated beam at the first width and a first set of post-patient x-ray apertures for shielding the detector from scattered x-rays. Additionally, the source/detector overlap region has a second set of pre-patient x-ray apertures for collimating the x-ray fan beam into the second collimated beam at the second width and a second set of post-patient x-ray apertures for shielding the detector from scattered x-rays. The source-only region has a first set of pre-patient x-ray apertures for collimating the x-ray fan beam into the first collimated beam at the first width; and a second set of pre-patient x-ray apertures for collimating the x-ray fan beam into the second collimated beam at the second width.

The foregoing summary, as well as the following detailed description of certain embodiments of the present invention, will be better understood when read in conjunction with the appended drawings. For the purpose of illustrating the invention, there is shown in the drawings, certain embodiments. It should be understood, however, that the present invention is not limited to the arrangements and instrumentalities shown in the attached drawings.

DETAILED DESCRIPTION

Figure 1:
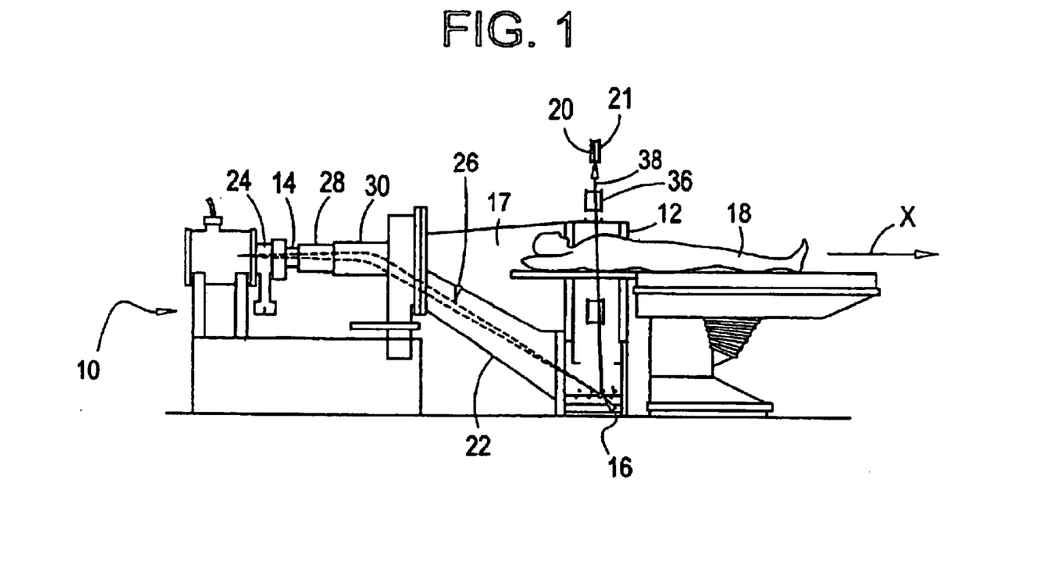
FIG. 1 is a transverse cross-sectional view of an electron beam tomography ("EBT") system, formed in accordance with an embodiment of the present invention.

FIG. 1 is a transverse cross-sectional view of an electron beam tomography ("EBT") system 10, formed in accordance with an embodiment of the present invention. The EBT system 10 includes an electron beam scan tube 12 having a cylindrical portion 14 and a semi-circular conical portion 17; and x-ray detector arrays 20 and 21. The scan tube 12 develops and projects an electron beam 26 towards a semi-circular ring-shaped target ("target ring") 16. The target ring 16 generates x-rays at portions thereof where the electron beam 26 impinges. The x-rays, after being collimated and subsequently passed through the patient 18 lying along a patient axis denoted by line X, are intercepted and detected by at least one of the detector arrays 20 and/or 21. A data output of the detector array 20 and/or 21 is processed by a computer system (not shown) to form diagnostic images and other information of interest to a physician and the patient.

Scan tube 12 includes a vacuum envelope 22, which houses an electron gun 24 in the cylindrical portion 14. The electron gun 24 projects the axial electron beam 26 through the semi-circular conical portion 17. Focus coils 28 magnetically focus the electron beam 26 to a spot, which impinges on the target ring 16. Bending coils 30 provide a magnetic field to bend the electron beam 26 so that it is directed through the semi-circular conical portion 17 toward the target ring 16.

The bending coils 30 not only deflect the electron beam 26, but also rapidly and repeatedly sweep the electron beam 26 arcuately along the target ring 16 so as to create a source of x-rays that rotates substantially within a single plane. A collimator assembly 36 (shown in FIGS. 3–7) is disposed in the beam path between the target ring 16 and the detector arrays 20 and 21 so as to block the unwanted x-rays emitted by the target ring 16 and to define an x-ray beam projected as a one to ten millimeter thick planar fan beam. A sector of the x-ray fan beam is detected by a portion of the x-ray detector array 20 and/or 21, which provide measured values to the computer in response thereto.

Figure 2:
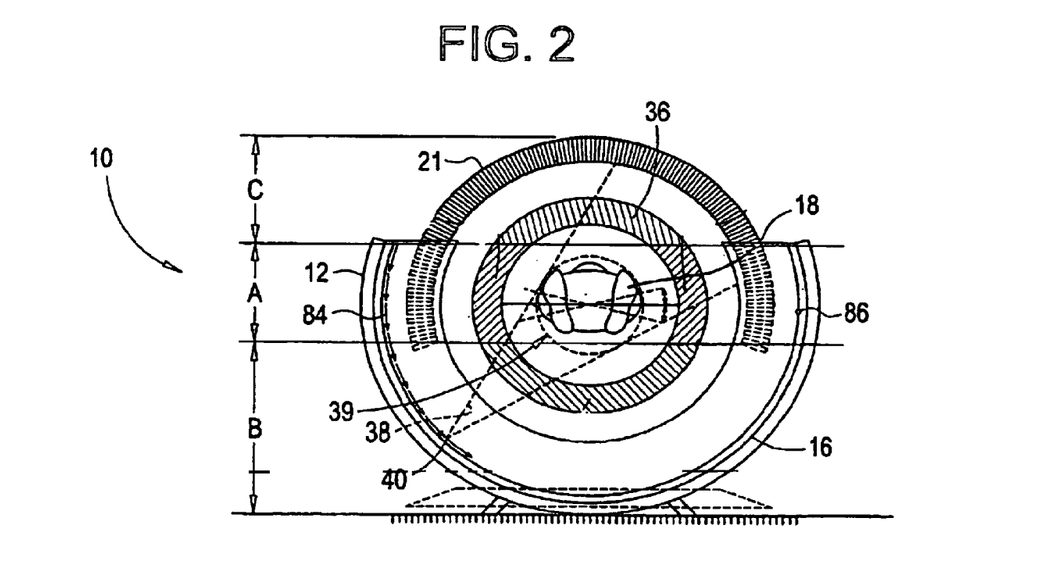
FIG. 2 is an axial cross-sectional view of an electron beam tomography ("EBT") system, formed in accordance with an embodiment of the present invention.

FIG. 2 is an axial cross-sectional view of an electron beam tomography ("EBT") system 10, formed in accordance with an embodiment of the present invention. By way of example, the collimator assembly 36 may be donut or circular shaped to surround the scan field 39. The collimator assembly 36 collimates x-rays projecting from the target ring 16 and projecting onto the detector arrays 20 and 21. As shown in FIG. 2, only detector array 21 is visible, as detector array 20 is positioned behind and adjacent to detector array 21. The x-ray fan beam 38 is shown emanating from beam spot 40. That is, the electron beam 26 impinges on the target ring 16 at the beam spot 40, which in turn generates the x-ray fan beam 38. The target ring 16 and the detector arrays 20 and 21 overlap at an overlap region A. The source-only region of the EBT system 10 is denoted by the source-only region B; while the detector-only region is denoted by the detector-only region C.

Figure 3:
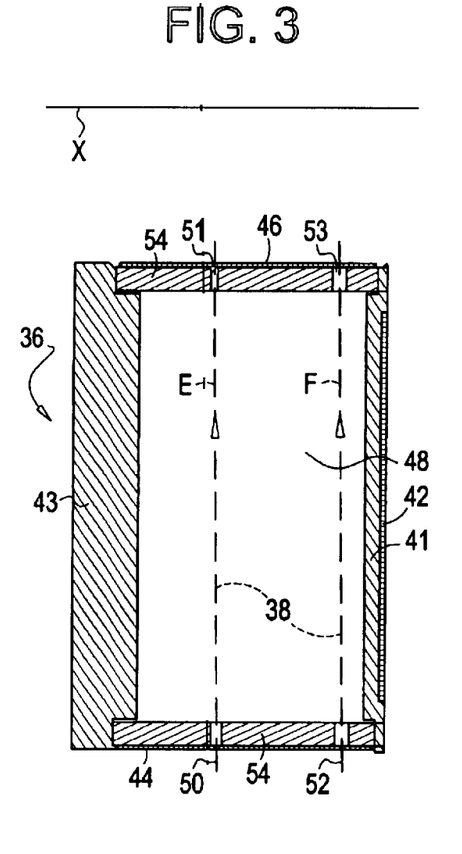
FIG. 3 is a cross-sectional view in a plane that contains axis line X in FIG. 1 of the collimator in the source-only region, formed in accordance with an embodiment of the present invention.
Figure 4:
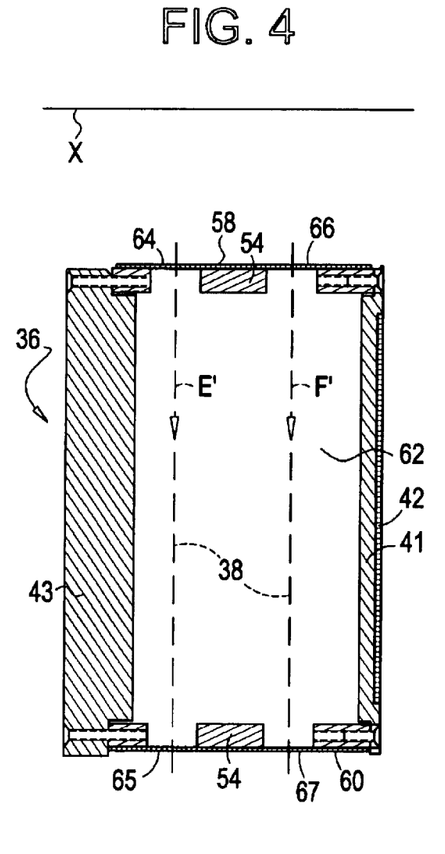
FIG. 4 is a cross-sectional view in a plane that contains axis line X in FIG. 1 of the collimator in the detector-only region, formed in accordance with an embodiment of the present invention.
Figure 5:
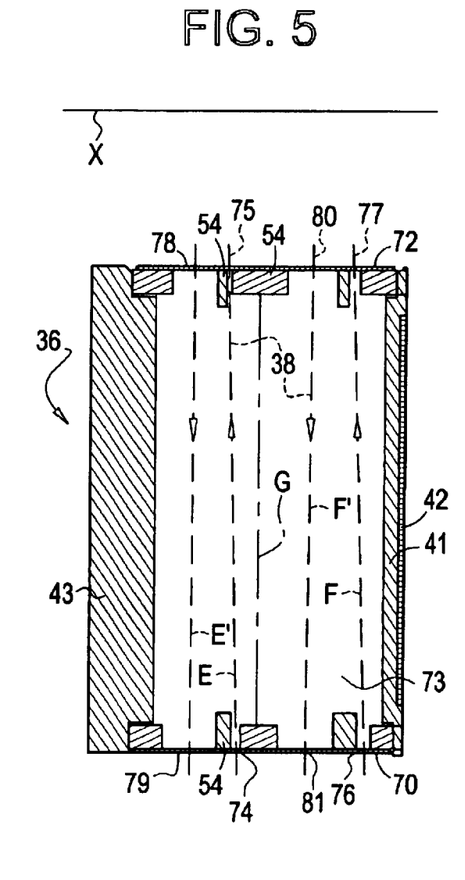
FIG. 5 is a cross-sectional view in a plane that contains axis line X in FIG. 1 of the collimator in the detector/source overlap region, formed in accordance with an embodiment of the present invention.

FIG. 3 is a cross-sectional view in a plane that contains axis line X of the collimator assembly 36 in the source-only region B, formed in accordance with an embodiment of the present invention. FIG. 4 is a cross-sectional view in a plane that contains axis line X of the collimator assembly 36 in the detector-only region C, formed in accordance with an embodiment of the present invention. FIG. 5 is a cross-sectional view in a plane that contains axis line X of the collimator assembly 36 in the overlap region A, formed in accordance with an embodiment of the present invention.

Turning now to FIG. 3, the portion of the collimator assembly 36 in the source-only region B includes first and second rings 41 and 43, a cover 42 over the first ring 41, a first pre-patient x-ray surface 44, a second pre-patient x-ray surface 46 and an inner cavity 48 therebetween. The first pre-patient x-ray surface 44 includes a first x-ray inlet aperture 50 and a second x-ray inlet aperture 52. The second pre-patient x-ray surface 46 includes a first x-ray outlet aperture 51 and a second x-ray outlet aperture 53. The first and second pre-patient x-ray surfaces 44 and 46 may be covered by Lexan®, or any other material that allows x-rays to pass through, while at the same time, maintaining the structural integrity of the collimator assembly 36. The x-ray fan beam 38 is generated from the target ring (not shown in FIG. 3) toward the patient axis X, as shown by the arrows of beams E and F. The x-ray fan beam is collimated through the apertures formed between the blocking portions 54. The blocking portions 54 may be formed of steel, lead, brass, or other materials that impede the progress of x-rays. The x-ray fan beam 38 may pass through the apertures 50–53, but is blocked by the blocking portions 54. Also, the x-ray fan beam 38 is collimated through the source-only region B before the x-ray fan beam 38 passes through the patient. That is, as discussed below, the x-ray fan beam 38 passes through the collimator assembly 36 in the source-only region B before the x-ray fan beam 38 encounters the patient along the axis denoted by line X and the portion of the collimator assembly 36 in the detector-only region C.

The collimator assembly 36 may be positioned such that the following tomographic slices ("slices") may be used to image a patient: (1.) one intermediate slice on one detector array 21 ("one intermediate slice"); (2.) one thin slice on detector array 20 and one thin slice on detector array 21 ("two thin slices"); (3.) one thick slice on both detector arrays 20 and 21 ("one thick slice"); or (4.) one intermediate slice on detector array 20 and one intermediate slice on detector array 21 ("two intermediate slices"). The "one thick slice" is obtained by using the same collimator position as the "two intermediate slices," but the outputs of the two detectors 20 and 21 are added either electrically or digitally. By way of example only, the thick, intermediate and thin slices may range in width from 10 mm to 1 mm. The slice widths depend on the widths of the apertures 51 and 53. The apertures 50–53 may be sized differently to accommodate different sized slices.

For example, if the collimator assembly 36 is set in a first position, the x-ray fan beam (the center of which is represented by reference line E) may pass through the first x-ray inlet aperture 50, through the inner cavity 48, and then through the first x-ray outlet aperture 51. Then, the x-ray fan beam 38 passes through the patient 18 lying along the axis denoted by line X, then through the collimator assembly 36 at the detector-only region A, until it impinges on one or both of the detector arrays 20 or 21. Because FIG. 3 only shows the collimator assembly 36 in the source only region B, the x-ray fan beam 38 that passes through the collimator assembly 36 in the source-only region B has yet to pass through the patient 18. If the collimator assembly 36 is positioned to obtain one intermediate slice the collimated x-ray fan beam 38 impinges on detector array 21 when the cone angle of the x-ray fan is minimized. If, however, the collimator assembly 36 is positioned to obtain two equal width slices, such as two thin slices, one half of the collimated x-ray fan beam 38 impinges on the first detector array 20, while the second half of the collimated x-ray fan beam 38 impinges on the second detector array 21.

The collimator assembly 36 may also be mechanically shifted, either through an actuator, an operator, or the like, to a second position such that the x-ray fan beam 38 may pass through the second x-ray inlet aperture 52 to the second x-ray oulet aperture 53 (with the center of the x-ray fan beam 38 being denoted by reference line F). The second x-ray inlet aperture 52 may be a different size than the first x-ray inlet aperture 50 and the second x-ray outlet aperture 53 may be a different size than the first x-ray outlet aperture 51. Thus, different size slices may be obtained depending upon whether the first or second x-ray inlet and outlet apertures 50 and 51 or 52 and 53 are used, which is determined by the position of the collimator assembly 36. That is, the collimator assembly 36 may be in a first position to obtain a first single slice (such as the single intermediate slice if the x-ray fan beam 38 passes through the first x-ray inlet aperture 50 and first x-ray outlet aperture 51), a second position to obtain a first double slice (such as two thin slices if the x-ray fan beam 38 passes through the first x-ray inlet and outlet apertures 50 and 51, respectively); a third position to obtain a second single slice (such as the single thick slice if the x-ray fan beam 38 passes through the second x-ray inlet aperture 52 and the second x-ray outlet aperture 53); and the third position to obtain a second double slice (such as two intermediate slices if the x-ray fan beam 38 passes through the second x-ray inlet and outlet apertures 52 and 53, respectively). Thus, the collimator assembly 36 may be moved, actuated, or otherwise shifted through multiple positions to obtain different slice thicknesses and combinations. The detector assembly (including detector arrays 20 and 21) is also positioned differently for each collimator assembly 36 position.

The collimator assembly 36 may be shifted through three different positions, while the detector arrays 20 and 21 are shifted through two different positions to provide four different slice configurations. That is, the collimator assembly 36 may be in a first position, while the detector arrays are in a first position to provide a first slice configuration. The collimator assembly 36 may be in a second position, while the detector arrays 20 and 21 are in a second position to provide a second slice configuration. Further, the collimator assembly 36 may be in a third position, while the detector arrays 20 and 21 are in the second position to provide a third and fourth slice configurations.

With respect to FIG. 4, the portion of the collimator assembly 36 in the detector-only region C includes the first ring 41, the cover 42 and second ring 43. Additionally, the collimator assembly 36 in the detector-only region C includes a first post-patient x-ray surface 58, a second post-patient x-ray surface 60 and an inner cavity 62. The first post-patient x-ray surface 58 includes a first x-ray inlet aperture 64 and a second x-ray inlet aperture 66. The second post-patient x-ray surface 60 includes a first x-ray outlet aperture 65 and a second x-ray outlet aperture 67. The first and second post-patient x-ray surfaces 58 and 60 may be covered with Lexan®, or any other material that allows x-rays to pass through, while at the same time, maintaining the structural integrity of the collimator assembly 36. The x-ray fan beam 38 passes through the collimator assembly 36 in the detector-only region C after the x-ray fan beam 38 passes through the source-only region B and the patient lying along the axis X. It is noted that E' and F' represent that the x-ray fan beam 38 has passed through the patient lying along the axis X; whereas E and F, as shown in FIG. 3, represent that the x-ray fan beam 38 has not yet passed through the patient. Additionally, once the x-ray fan beam 38 has encountered the collimator assembly 36 in the source-only region B, the x-ray fan beam 38 is a collimated beam. That is, the collimator assembly 36 collimates the x-ray fan beam 38 into a collimated beam.

The x-ray fan beam 38 passes through the patient lying along the axis X. After passing through the patient, the x-ray fan beam 38 passes through the first post-patient x-ray surface 58, through the inner cavity 62, and then through the second post-patient x-ray surface 60. As mentioned above, the blocking portions 54 may be formed of steel, lead, brass, or other materials that impede the progress of x-rays. The collimated x-ray fan beam 38 may pass through the apertures 64–67. The blocking portions 54 prevent scattered x-rays from reaching the detector arrays 20 and 21.

As discussed above, the collimator assembly 36 may be positioned such that the following tomographic slices may be used to image a patient: (1.) one intermediate slice; (2.) two thin slices; (3.) one thick slice; or (4.) two intermediate slices. The slice thickness depends on the width of the apertures 51 and 53. The apertures 64–67 may be sized differently to accommodate different size slices. For example, if the collimator is set in a first position, the x-ray fan beam (the center of which is represented by reference line E') may pass through the first x-ray inlet aperture 64, then through the inner cavity 62, and through the x-ray outlet aperture 65. Then, the x-ray fan beam 38 impinges on one or both of the detector arrays 20 or 21. Because FIG. 4 only shows the collimator assembly 36 in the detector-only region C, the x-ray fan beam 38 that passes through the collimator assembly 36 in the detector-only region C has already passed through the patient 18. If the collimator assembly 36 is positioned to obtain one slice, such as a 3 mm slice, the collimated x-ray fan beam 38 impinges on one detector array 21. If, however, the collimator assembly 36 is positioned to obtain two equal width slices, such as two thin slices, one half of the collimated x-ray fan beam 38 impinges on the first detector array 20, while the second half of the collimated x-ray fan beam 38 impinges on the second detector array 21.

The collimator assembly 36 may also be shifted to a second position such that the x-ray fan beam 38 may pass from the second x-ray inlet aperture 66 to the second x-ray outlet aperture 67 (with the center of the x-ray fan beam 38 being denoted by reference line F'). The second x-ray inlet aperture 66 may be a different size than the first x-ray inlet aperture 64; while the second x-ray outlet aperture 67 may be a different size than the first x-ray outlet aperture 65. Thus, different sized slices may be accommodated depending on the position of the collimator assembly 36. That is, the collimator assembly 36 may be in a first position to obtain one intermediate slice (when the x-ray fan beam 38 passes through the first x-ray inlet aperture 64 and the first x-ray outlet aperture 65), a second position to obtain two thin slices (when the x-ray fan beam 38 passes through the first x-ray inlet and outlet apertures 64 and 65, respectively); a third position to obtain one thick slice (when the x-ray fan beam 38 passes through the second x-ray inlet aperture 66 and second x-ray outlet aperture 67); and the same third position to obtain two intermediate slices (when the x-ray fan beam 38 passes through the second x-ray inlet and outlet apertures 66 and 67, respectively).

Additionally, the apertures 64–67 are wider than the apertures 50–53 to accommodate the width of the x-ray fan beam 38. That is, the collimated x-ray fan beam 38 is wider near the detector arrays 20 and 21 than by the target ring 16, which is the x-ray source.

With respect to FIG. 5, the portion of the collimator assembly 36 in the overlap region A includes the first ring 41, the second ring 43, and the cover 42 over the first ring 41. Additionally, the collimator assembly 36 in the overlap region A includes a first x-ray surface 70, a second x-ray surface 72 and an inner cavity 73. The x-ray surface 44, 60 and 70 are physically the same cylindrical surface; and x-ray surface 46, 58 and 72 are physically a second cylindrical surface. Cavities 48, 62 and 73 are the same donut shaped cavity. Each aperture pair 50, 74; 51, 75; 52, 76; 53, 77; 64, 78; 65, 79; 66, 80 and 67, 81 is physically a single continuous aperture. The first x-ray surface 70 includes a first pre-patient x-ray inlet aperture 74, a second pre-patient x-ray inlet aperture 76, a first post-patient x-ray outlet aperture 79, and a second post-patient x-ray outlet aperture 81. The second x-ray surface 72 includes a first pre-patient x-ray outlet aperture 75, second pre-patient x-ray outlet aperture 77, a first post-patient x-ray inlet aperture 78 and a second post-patient x-ray inlet aperture 80. Because the collimator assembly 36 is positioned within the overlap region A, the portion of the collimator within the overlap region A includes x-ray inlet and outlet apertures on both x-ray surfaces 70 and 72 to accommodate the sweeping of the x-ray fan beam 38. That is, at a first radial angle, the x-ray fan beam 38 passes through the collimator assembly 36 in the overlap region A before it passes through the patient 18 lying along the axis X. However, when the x-ray fan beam 38 is radially rotated toward the other side of the collimator assembly 36, the same portion of the collimator assembly 36 in the overlap region receives the x-ray fan beam 38 after the x-ray fan beam 38 passes through the patient 18 lying along the axis X. For example, as shown in FIG. 2, the beam spot (i.e., the point from which the x-ray fan beam 38 emanates) may be at the position marked by reference numeral 84. The beam spot may then be swept to a position denoted by reference numeral 86. Thus, the collimator assembly 36 includes corresponding apertures to accommodate both pre and post patient x-ray fan beams.

Referring again to FIG. 5, the first and second x-ray surfaces 70 and 72 may be covered with Lexan®, or any other material that allows x-rays to pass through, while at the same time, maintaining the structural integrity of the collimator assembly 36. The x-ray fan beam 38 passes between the apertures as described above with respect to FIG. 3 and 4. For example, for one intermediate slice or two thin slices, the x-ray fan beam 38 (the center of which is denoted by line E, for a pre-patient x-ray fan beam 38) passes from the first pre-patient x-ray inlet aperture 74 to the first pre-patient x-ray outlet aperture 75. The x-ray fan beam 38 then passes through the patient and encounters the other side of the collimator assembly 36 in the overlap region, such that the x-ray fan beam passes between an analogous first post-patient x-ray inlet aperture 78' to an analogous first post-patient x-ray outlet aperture 79' (the center of the post-patient beam is denoted by reference line E').

For one thick slice or two intermediate slices, the collimator assembly 36 is shifted such that the x-ray fan beam 38 passes from the second pre-patient x-ray inlet aperture 76 to the second pre-patient x-ray outlet aperture 77. The x-ray fan beam 38 then passes through the patient lying along the axis X. After passing through the patient, the x-ray fan beam 38 encounters the corresponding other side of the collimator assembly 36 in the overlap region A such that the post patient x-ray fan beam 38 passes from an analogous second post-patient x-ray inlet aperture 80' to an analogous second post-patient x-ray outlet aperture 81'. In general, if a pre-patient x-ray fan beam 38 impinges on the collimator assembly 36 in the overlap region A, the resulting post-patient x-ray fan beam 38 impinges on the other side of the collimator assembly 36 in the overlap region A.

Figure 6:
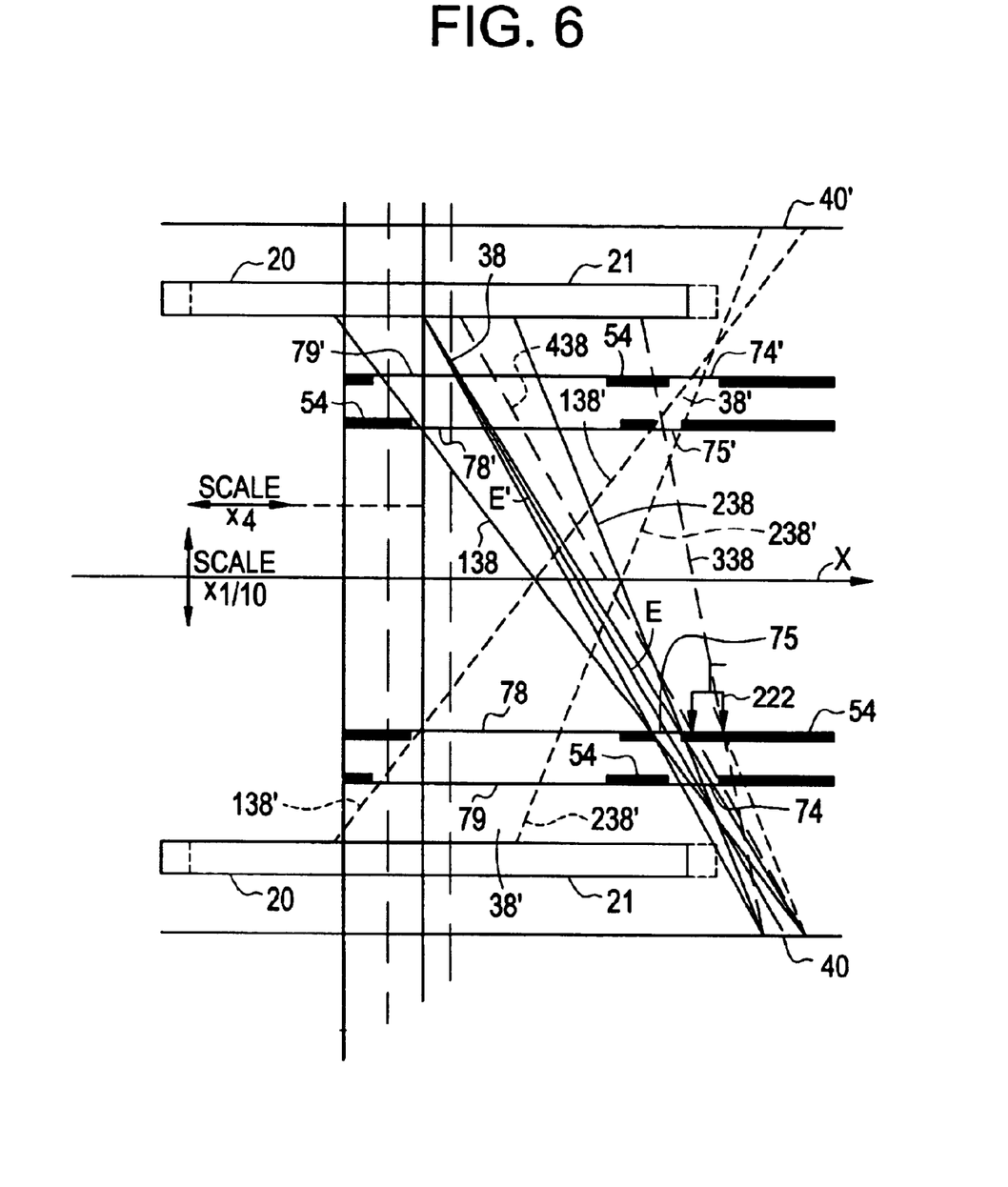
FIG. 6 is a cross-sectional view in a plane that contains axis line X in FIG. 1 of both sides of the collimator in the overlap region, formed in accordance with an embodiment of the present invention.

FIG. 6 is a cross-sectional view in a plane that contains axis line X of FIG. 1 of both sides of the collimator assembly 36 in the overlap region A, formed in accordance with an embodiment of the present invention. As noted in FIG. 6, the horizontal scale is approximately 4:1, while the vertical scale is approximately 1:10. FIG. 6 represents the one intermediate slice and two thin slice portion of the EBT system 10. The narrower the slice width, the better the axial resolution (narrower slice widths also result in reduced dosage to the patient). FIG. 6 illustrates the EBT system 10 on the left side of reference line G, shown in FIG. 5. The patient 18 lies along the axis X. The x-ray fan beam 38 emanates from the beam spot 40. The x-ray fan beam 38 has sides 138 and 238. The x-ray fan beam 38 passes from the first pre-patient x-ray inlet aperture 74 through the first pre-patient x-ray outlet aperture 75. The x-ray fan beam 38 then passes through the patient lying along the axis X. The x-ray fan beam 38 then passes through the first post-patient x-ray inlet aperture 78' on through the first post-patient x-ray outlet aperture 79'.

As shown in FIG. 6, the apertures 74, 75, 78, 79 (and 74', 75', 78' and 79') are formed such that the x-ray fan beam 38 impinges on the detector array(s) at a first intermediate width. When the collimator assembly 36 is in a first position, as shown in FIG. 6, one half of the x-ray fan beam 38 impinges on the first detector 20, while the other half of the x-ray fan beam 38 impinges on the second detector 21 (thus, two thin slices are detected). However, the collimator assembly 36 and detector arrays 20 and 21 may be shifted to a second position such that x-ray fan beam 38 impinges only on the second detector 21 (resulting in one intermediate slice). For example, reference slot 222 shows where the first pre-patient x-ray outlet 75 shifts (thus, the other apertures would also shift), for the x-ray fan beam defined by sides 338 and 438 to impinge solely on the second detector 21. Additionally, the x-ray fan beam 38 may be swept through a 180 degree radial arc such that the x-ray fan beam 38' emanates from beam spot 40'. In this case, the electron fan beam 38' is defined by sides 138' and 238'.

Figure 7:
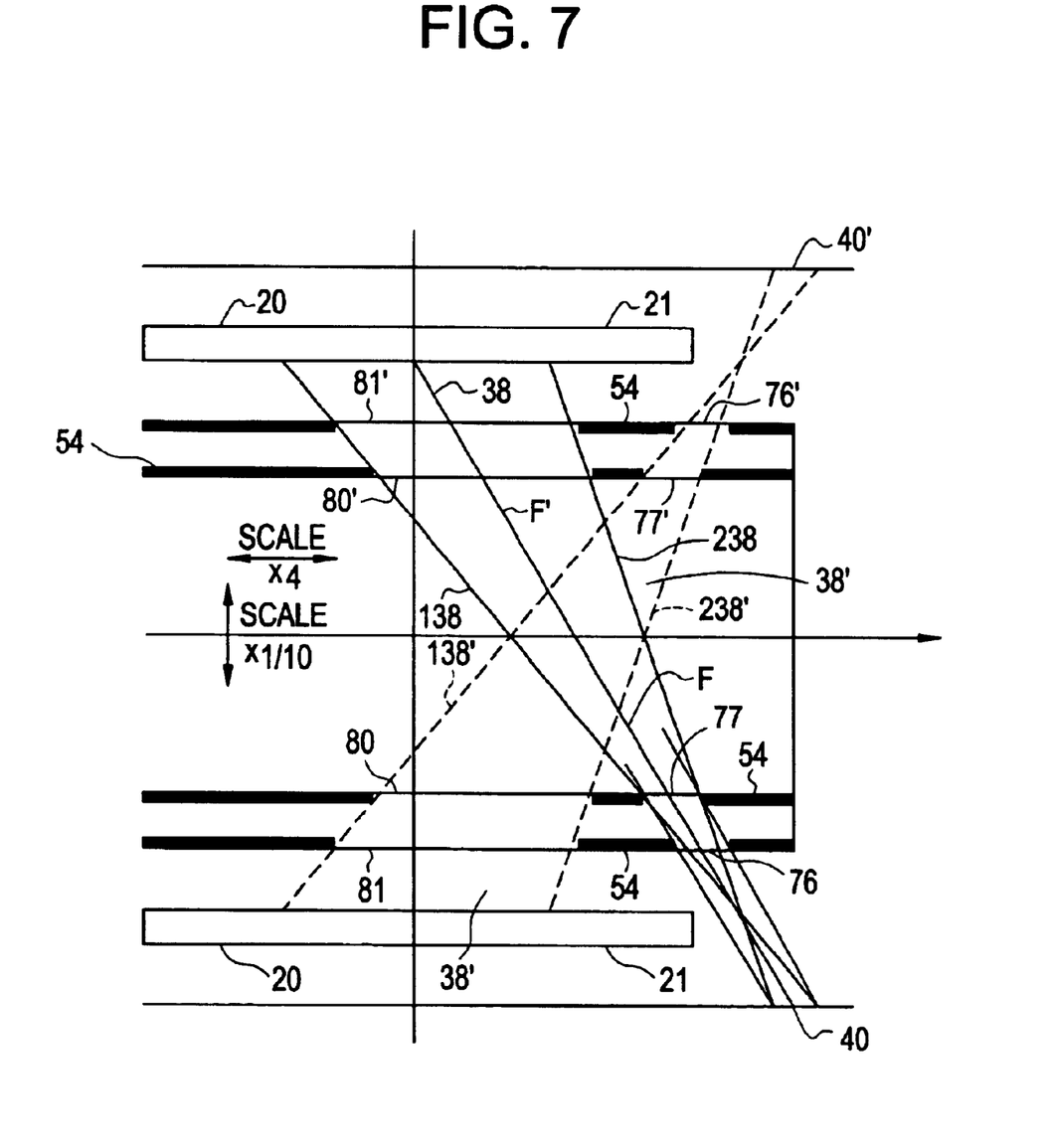
FIG. 7 is a cross-sectional view in a plane that contains axis line X in FIG. 1 of both sides of the collimator in the overlap region, formed in accordance with an embodiment of the present invention.

FIG. 7 is a cross-sectional view of both sides of the collimator assembly 36 in the overlap region A, formed in accordance with an embodiment of the present invention. As noted in FIG. 6, the horizontal scale is approximately 4:1, while the vertical scale is approximately 1:10. FIG. 7 represents the one thick slice and two intermediate slice portions of the EBT system 10. That is, FIG. 7 illustrates the EBT system 10 on the right side of reference line G, shown in FIG. 5. The patient 18 lies along the axis X. The x-ray fan beam 38 emanates from the beam spot 40. The x-ray fan beam 38 has sides 138 and 238. The x-ray fan beam 38 passes from the second pre-patient x-ray inlet aperture 76 through the first pre-patient x-ray outlet aperture 77. The x-ray fan beam 38 then passes through the patient lying along the axis X. The x-ray fan beam 38 then passes through the second post-patient x-ray inlet aperture 80' on through the second post-patient x-ray outlet aperture 81'. As shown in FIG. 7, the apertures 76, 77, 80 and 81; (and 76', 77', 80' and 81') are formed such that the x-ray fan beam 38 impinges on the detector array(s) at a thick width. When the collimator assembly 36 is in the position, as shown in FIG. 7, one half of the x-ray fan beam 38 impinges on the first detector 20, while the other half of the x-ray fan beam 38 impinges on the second detector 21 (resulting in two intermediate slices). However, data from the two detector arrays 20 and 21 may be added resulting in one thick slice. Additionally, the x-ray fan beam 38 may be swept through a 180 degree arc such that the x-ray fan beam 38' emanates from beam spot 40'. In this case, the electron fan beam 38' is defined by sides 138' and 238'.

The collimator assembly 36 of the EBT system 10 is not limited to the slice configurations described above. A wide variety of slice configurations, in addition to the one thick, two intermediate, one intermediate, and two thin slice configurations, may be implemented within the system. Additionally, the collimator may include more apertures that may allow for an increased number of slice configurations. For example, the collimator may include more than two sets of x-ray inlet and outlet apertures. That is, the collimator may include a set of apertures for one thick/two intermediate slices, another set of apertures for one intermediate/two thin slices, another set of apertures for one thin slice/two very thin slices, etc. Also, additionally, more than two detector arrays may be used. For example, instead of having two detector arrays aligned with, and adjacent one another, three or more detector arrays may be utilized. Also, multiple target rings may be used within the EBT system.

Thus, embodiments of the present invention provide a more efficient (and less expensive) dual-slice EBT scanner, because a single collimator may be used to collimate an x-ray fan beam at a plurality of slice widths.

While the invention has been described with reference to certain embodiments, it will be understood by those skilled in the art that various changes may be made and equivalents may be substituted without departing from the scope of the invention. In addition, many modifications may be made to adapt a particular situation or material to the teachings of the invention without departing from its scope. Therefore, it is intended that the invention not be limited to the particular embodiment disclosed, but that the invention will include all embodiments falling within the scope of the appended claims.

What is claimed is:

1. An electron beam tomography (EBT) scanning system comprising:
    an electron source generating an electron beam;
    a target ring that receives said electron beam from said electron source, said target ring emitting an x-ray fan beam upon impingement of the electron beam on said target ring;
    a pair of detector arrays arranged opposite said target ring detecting said x-ray fan beam; and
    a collimator having at most two collimator rings, said collimator arranged concentrically between said target ring and said pair of detector arrays, said collimator having interior and exterior walls concentrically arranged with one another and surrounding a patient examination area, said interior and exterior walls having first and second sets of apertures aligned to collimate said x-ray fan beam into a first collimated beam having a first width and a second collimated beam having a second width, respectively, said first and second collimated beams forming at least one of a single and double tomographic slice, and said first and second collimated beams being detected by at least one of said pair of detector arrays.

2. The EBT scanning system of claim 1, said collimator being moved between first and second positions with respect to said target ring to define said first and second collimated beams having said first and second widths, respectively.

3. The EBT scanning system of claim 1 wherein said collimator is moved between first and second positions with respect to said target ring to direct said first collimated beam solely onto one detector of said pair of detectors when in said first position, and onto both detectors of said pair of detector arrays when in said second position.

4. The EBT scanning system of claim 1 wherein said collimator includes a detector-only region having a first set of post-patient x-ray apertures for shielding said pair of detector arrays from scattered x-rays; and a second set of post-patient x-ray apertures for shielding said pair of detector arrays from scattered x-rays.

5. The EBT scanning system of claim 1 wherein said collimator comprises a source/detector overlap region having a first set of pre-patient x-ray apertures for collimating said x-ray fan beam into said first collimated beam at said first width and a first set of post-patient x-ray apertures for shielding said pair of detector arrays from scattered x-rays; and a second set of pre-patient x-ray apertures for collimating said x-ray fan beam into a second collimated beam at a second width and a second set of post-patient x-ray apertures for shielding said pair of detector arrays from scattered x-rays.

6. The EBT scanning system of claim 1 wherein said collimator includes a source-only region having a first set of pre-patient x-ray apertures for collimating said x-ray fan beam into said first collimated beam at said first width; and a second set of pre-patient x-ray apertures for collimating said x-ray fan beam into a second collimated beam at a second width.

7. An electron beam tomography (EBT) scanning system comprising:
    an electron source generating an electron beam;
    a single target ring that receives said electron beam from said electron source, said target ring emitting an x-ray fan beam upon impingement of the electron beam on said target ring;
    a first detector array and a second detector array, said first and second detector arrays arranged opposite said single target ring detecting said x-ray fan beam; and
    a collimator having at most two collimator rings, said collimator arranged concentrically between said target ring and said first and second detector arrays, said collimator having interior and exterior walls concentrically arranged with one another and surrounding a patient examination area, said interior and exterior walls having:
        a first set of apertures aligned to collimate said x-ray fan beam into a first collimated beam having a first width, said first collimated beam being detected by said first and second detector arrays; and
        a second set of apertures aligned to collimate said x-ray fan beam into a second collimated beam having a second width, said second collimated beam being detected by said first and second detector arrays, said collimator being moved between first and second positions with respect to said single target ring to define said first and second collimated beams having said first and second widths, respectively.

8. The EBT scanning system of claim 7 wherein said collimator is moved into a third position with respect to said target ring to direct said first collimated beam having said first width solely onto one of said first and second detector arrays.

9. The EBT scanning system of claim 7 wherein said collimator includes a detector-only region having a first set of post-patient x-ray apertures for shielding the pair of detector arrays from scattered x-rays; and a second set of post-patient x-ray apertures for shielding the pair of detector arrays from scattered x-rays.

10. The EBT scanning system of claim 7 wherein said collimator comprises a source/detector overlap region having a first set of pre-patient x-ray apertures for collimating said x-ray fan beam into said first collimated beam at said first width and a first set of post-patient x-ray apertures for shielding the pair of detector arrays from scattered x-rays; and a second set of pre-patient x-ray apertures for collimating said x-ray fan beam into a second collimated beam at a second width and a second set of post-patient x-ray apertures for shielding the pair of detector arrays from scattered x-rays.

11. The EBT scanning system of claim 7 wherein said collimator includes a source-only region having a first set of pre-patient x-ray apertures for collimating said x-ray fan beam into said first collimated beam at said first width; and a second set of pre-patient x-ray apertures for collimating said x-ray fan beam into a second collimated beam at a second width.

12. A collimator in, an electron beam tomography (EBT) system, said EBT system having a target ring emitting an x-ray fan beam and first and second detector arrays detecting a collimated region of the x-ray fan beam, said collimator comprising:
at most two collimator rings; and
interior and exterior walls concentrically arranged with one another and surrounding a patient examination area, said interior and exterior walls having:
a first set of apertures aligned to collimate an x-ray fan beam into a first collimated beam having a first width, said first collimated beam being detected by first and second detector arrays when said collimator is in a first position, said first collimated beam being detected by one of said first and second detector arrays when said collimator is moved to a second position; and
a second set of apertures aligned to collimate said x-ray fan beam into a second collimated beam having a second width, said second collimated beam being detected by said first and second detector arrays when said collimator is moved to a third position, and said collimator being moved between said first, second, and third positions with respect to said target ring to define said first and second collimated beams having said first and second widths, respectively.

13. The collimator of claim 12 wherein said collimator includes a detector-only region having a first set of post-patient x-ray apertures for shielding the pair of detector arrays from scattered x-rays; and a second set of post-patient x-ray apertures for shielding the pair of detector arrays from scattered x-rays.

14. The collimator of claim 12 wherein said collimator comprises a source/detector overlap region having a first set of pre-patient x-ray apertures for collimating said x-ray fan beam into said first collimated beam at said first width and a first set of post-patient x-ray apertures for shielding the pair of detector arrays from scattered x-rays; and a second set of pre-patient x-ray apertures for collimating said x-ray fan beam into a second collimated beam at a second width and a second set of post-patient x-ray apertures for shielding the pair of detector arrays from scattered x-rays.

15. The collimator of claim 12 further including a source-only region having a first set of pre-patient x-ray apertures for collimating said x-ray fan beam into said first collimated beam at said first width; and a second set of pre-patient x-ray apertures for collimating said x-ray fan beam into a second collimated beam at a second width.

16. An electron beam tomography (EBT) scanning system comprising:
an electron source generating an electron beam;
a target ring that receives said electron beam from said electron source, said target ring emitting an x-ray fan beam upon impingement of the electron beam on said target ring;
a first detector array and a second detector array, said first and second detector arrays arranged opposite said target ring detecting said x-ray fan beam; and
a collimator having at most two collimator rings, said collimator arranged concentrically between said target ring and said first and second detector arrays, said collimator having interior and exterior walls concentrically arranged with one another and surrounding a patient examination area, said interior and exterior walls having:
a first set of apertures aligned to collimate said x-ray fan beam into a first collimated beam having a first width, said first collimated beam being detected by first and second detector arrays when said collimator is in a first position, said first collimated beam being detected by one of said first and second detector arrays when said collimator is moved to a second position; and
a second set of apertures aligned to collimate said x-ray fan beam into a second collimated beam having a second width, said second collimated beam being detected by said first and second detector arrays when said collimator is moved to a third position, and said collimator being moved between said first, second, and third positions with respect to said target ring to define said first and second collimated beams having said first and second widths, respectively.

17. The EBT scanning system of claim 16 wherein said collimator includes a detector-only region having a first set of post-patient x-ray apertures for shielding the pair of detector arrays from scattered x-rays; and a second set of post-patient x-ray apertures for shielding the pair of detector arrays from scattered x-rays.

18. The EBT scanning system of claim 16 wherein said collimator comprises a source/detector overlap region having a first set of pre-patient x-ray apertures for collimating said x-ray fan beam into said first collimated beam at said first width and a first set of post-patient x-ray apertures for shielding the pair of detector arrays from scattered x-rays; and a second set of pre-patient x-ray apertures for collimating said x-ray fan beam into a second collimated beam at a second width and a second set of post-patient x-ray apertures for shielding the pair of detector arrays from scattered x-rays.

19. The EBT scanning system of claim 16 wherein said collimator includes a source-only region having a first set of pre-patient x-ray apertures for collimating said x-ray fan beam into said first collimated beam at said first width; and a second set of pre-patient x-ray apertures for collimating said x-ray fan beam into a second collimated beam at a second width.

* * * * *